US008834850B2

(12) United States Patent
Busch et al.

(10) Patent No.: US 8,834,850 B2
(45) Date of Patent: Sep. 16, 2014

(54) INDUCED REMINERALISATION OF HUMAN DENTAL ENAMEL

(75) Inventors: Susanne Busch, Dresden (DE); Rüdiger Kniep, Langenfeld (DE)

(73) Assignee: Max-Planck-Gesellschaft zur Foerderung der Wissenschaten. e.V., Munich (DE)

( * ) Notice: Subject to any disclaimer, the term of this patent is extended or adjusted under 35 U.S.C. 154(b) by 1928 days.

(21) Appl. No.: 10/594,055

(22) PCT Filed: Nov. 11, 2005

(86) PCT No.: PCT/EP2005/012101
§ 371 (c)(1),
(2), (4) Date: Sep. 25, 2006

(87) PCT Pub. No.: WO2006/050966
PCT Pub. Date: May 18, 2006

(65) Prior Publication Data
US 2007/0218017 A1    Sep. 20, 2007

(30) Foreign Application Priority Data
Nov. 11, 2004    (DE) .......................... 10 2004 054 584

(51) Int. Cl.
| *A61K 8/00* | (2006.01) |
| *A61K 8/66* | (2006.01) |
| *A61K 6/00* | (2006.01) |
| *A61K 6/033* | (2006.01) |
| *A61K 6/027* | (2006.01) |
| *A61K 8/73* | (2006.01) |
| *A61K 8/19* | (2006.01) |
| *A61K 8/24* | (2006.01) |
| *A61K 8/65* | (2006.01) |
| *A61Q 11/00* | (2006.01) |

(52) U.S. Cl.
CPC ............... *A61K 6/033* (2013.01); *A61K 6/0008* (2013.01); *A61K 6/027* (2013.01); *A61K 8/731* (2013.01); *A61K 6/0017* (2013.01); *A61K 8/19* (2013.01); *A61K 2800/88* (2013.01); *A61K 8/24* (2013.01); *A61K 8/65* (2013.01); *A61Q 11/00* (2013.01)
USPC ............................................... 424/49; 424/50

(58) Field of Classification Search
None
See application file for complete search history.

(56) References Cited

U.S. PATENT DOCUMENTS

| 4,080,440 A | * | 3/1978 | DiGiulio et al. | ................. 424/49 |
| 4,397,837 A | * | 8/1983 | Raaf et al. | ......................... 424/51 |
| 6,010,684 A | * | 1/2000 | Wiedemann | ..................... 424/52 |
| 2003/0152528 A1 | * | 8/2003 | Singh et al. | ...................... 424/53 |

FOREIGN PATENT DOCUMENTS

| DE | 21 31 666 A | | 2/1972 |
| DE | 23 50 548 A | | 4/1974 |
| DE | 33 03 937 A | | 6/1984 |
| DE | 3303937 | * | 6/1984 |
| WO | WO 98/10736 A | | 3/1998 |
| WO | WO 03/099234 A | | 12/2003 |

* cited by examiner

*Primary Examiner* — Snigdha Maewall
(74) *Attorney, Agent, or Firm* — Rothwell, Figg, Ernst & Manbeck, P.C.

(57) ABSTRACT

The present application relates to the induced remineralization of human tooth enamel and in particular to the building up of apatite on tooth material.

26 Claims, No Drawings

INDUCED REMINERALISATION OF HUMAN DENTAL ENAMEL

CROSS REFERENCE TO RELATED APPLICATION

This application is a 35 USC §371 National Phase Entry Application from PCT/EP2005/012101, filed Nov. 11, 2005, and designating the United States.

The present application relates to the induced remineralization of human tooth enamel and in particular the building up of apatite on tooth material. The application also relates to the induced remineralization of human dentine and in particular the building up of dentine on tooth material.

Teeth are composite materials formed from apatite and proteins. They are very hard biomaterials based on calcium and phosphate. The tooth enamel, the outer layer of the crown of the tooth, is the hardest part of the tooth and contains no living cells. Tooth enamel consists of inorganic crystals, which have typical highly oriented arrangements. Tooth enamel is a tissue which, as soon as it is formed, remains unchanged almost for life, since the cells which are involved in the construction of the teeth die as soon as tooth formation is complete. Finished tooth enamel consists of approximately 95% by weight of apatite, approximately 3% by weight of proteins and lipids and approximately 2% by weight of water.

Dentine is the term for a hard substance which is related to bone and forms the core of the tooth in mammals and man. Dentine consists to the extent of approximately 30% of a cell-free organic base substance, in particular glycoproteins in which collagen fibers are incorporated. The inorganic constituents are predominantly hydroxylapatite, fluoroapatite and small amounts of carbonates, magnesium and trace elements.

In order to avoid or to repair damage to teeth, in particular by caries, it has been attempted for a long time to employ remineralizing systems. It was initially attempted here to improve the condition of the teeth by application of calcium phosphate compounds. Such single-component systems in which it is attempted to apply tooth material which has already been previously prepared, for example apatite, hydroxyapatite or other calcium phosphate compounds, to the teeth are described, inter alia, in EP 0 666 730 B1 or WO 01/95863. The problem of such systems is that treating tooth material with calcium phosphate compounds does not lead to growth of apatite which is structurally similar to the tooth material, but rather to a mere addition of apatite crystals to the tooth material, the apatite crystals having a morphology which is completely different from the tooth material. No strengthening of the tooth enamel or permanent filling of lesions is thus brought about, since the apatite crystals added do not have sufficient similarity and adhesion to the natural tooth material.

It was furthermore attempted with two-component systems to obtain a remineralization of teeth, the systems customarily comprising a calcium phase and a phosphate phase. Two-component systems are described, for example, in WO 98/10736 and DE 33 03 937 A1. It is disadvantageous with the procedures described there that the method described in WO 98/10736 combines calcium and phosphate solutions before application such that a metastable solution is formed from which apatite should crystallize out on the tooth. The method does not allow localized treatment on the tooth, since the reagent is employed as a mouthwash or gel which is massaged in using a toothbrush. Furthermore, the composite nature of the native enamel is not taken into account, since no organic component is contained in the system. The formation of tooth enamel-like crystallites is accordingly improbable. DE 33 03 937 describes a process in which calcium and phosphate ions are applied separately to the tooth in succession by immersing this in a cap which contains the corresponding ions in a gelatin matrix. With a recommended time of action of only two minutes, it is not to be expected that really relatively large amounts of apatite can be formed on the tooth surface. It is not confirmed using image material that the newly formed apatite layer contains enamel-like structures.

In further studies (S. Busch et al., Eur. J. Inorg. Chem. (1999), 1643-1653; S. Busch et al., Chem. Mater. 13 (2001), 3260-3271; S. Busch, Zahnärztliche Mitteilungen [Dental Communications] 91, No. 10 (2001), 34-38; R. Kniep et al., Angew. Chem. 108, No. 22 (1996), 2787-2791), the biomimetic morphogenesis of fluoroapatite gelatin composites was investigated. Biomimetic growth and self-organization of fluoroapatite aggregates by means of diffusion in denatured collagen matrices were observed here. The fundamental principles of fluoroapatite formation in gelatin gels was investigated here by means of double diffusion experiments of calcium and phosphate solutions in a U-tube. These studies describe the formation of fluoroapatite beads within the gel used.

WO 03/099234 A1 describes a process for the growth of apatite on tooth material, comprising the steps:
(i) application of a first gel which comprises gelatin and phosphate ions,
(ii) application of a second gel, the first layer of gel being covered with this second gel and
(iii) application of a medium containing calcium ions,
a building up of apatite on the surface of the tooth material being caused.

Good results could already be obtained with this process. It was desirable, however, for this process to be further improved, in particular with respect to the growth rate of the apatite layer.

It was therefore an object of the present application to make available a process with which defects on tooth material can be repaired by remineralization with a high growth rate.

This object is achieved according to the invention by the use
(i) of an alkaline medium,
(ii) of a first gel which comprises gelatin and phosphate ions, and
(iiia) of a second gel which is free of phosphate ions, the first layer of gel being covered with this second gel and/or
(iiib) of a medium containing calcium ions, for the production of a composition or of a kit for the growth of apatite on tooth material.

Surprisingly it has been found that by pretreating the tooth material with an alkaline medium it is possible to achieve a distinct increase in the growth rate of fluoroapatite on tooth samples, especially human tooth samples. In particular it has been possible to achieve growth rates of 1 to 5 μm/day, in particular of 3 to 5 μm/day.

With preference in accordance with the invention the alkaline medium used is an alkaline solution, in particular an aqueous alkaline solution, or an alkaline gel. This alkaline medium preferably has a pH of 7.1 to 14, in particular of at least 7.3, more preferably at least 7.5 and most preferably of at least 8, and preferably up to 10, more preferably up to 9. With particular advantage the alkaline medium used is a composition which is compatible in the human oral cavity, such as a 0.05 to 1N NaOH solution, for example. It has been found that the alkaline medium, and especially aqueous sodium hydroxide solution, may further, advantageously, already contain calcium ions—for example, 10 to 50% of a 0.1 to 0.3N $CaCl_2$ solution.

According to the invention, it is possible to achieve a real growth of tooth enamel-like material. A significant advantage consists in the fact that a high order of small apatite needles is obtained, which structurally have a great similarity to native tooth enamel. With appropriate substrate orientation, virtually no difference can be detected between apatite which has grown and original tooth material.

In a further embodiment it is possible, according to the invention, to remineralize dentine. In this case growth of dentine layers or dentine-like layers on tooth material can be achieved. The grown layer corresponds to natural dentine in terms of crystallite size and crystallite arrangement.

Further advantages of the invention are that a real growth of the fluoroapatite crystallites on the tooth substrate can be assumed. The Vickers hardness of this novel layer corresponds to that of natural enamel or natural dentine. Carrying out the individual steps is so simple that the remineralization of tooth enamel or the remineralization of dentine can in principle be carried out by the patient himself. The gel can be applied locally to the damaged sites and solidifies there. Since the warmed gel cools very rapidly, waiting times between the individual steps are barely necessary.

Since the softening temperature of the gel is somewhat above normal body temperature (38 to 42° C.), melting of the gel during the period of action is prevented. Uncontrolled mineralization can thus be avoided.

In accordance with the invention, apatite is grown onto tooth material by
(i) applying an alkaline medium, and
(ii) applying a first gel, which comprises gelatine and also phosphate ions, to the tooth material pretreated with the alkaline medium.

Furthermore, in accordance with the invention, one of steps (iiia) or (iiib), or both steps, is or are carried out, namely the application of a second gel, which is free from phosphate ions, this second gel covering the first gel layer, and/or the application of a medium containing calcium ions. Particularly when using a calcium ions-containing gel as the medium containing calcium ions, this gel can be applied directly (i.e. without treatment with the gel (iiia)) to the first gel.

In accordance with the invention it has additionally been found that through the use of a first gel which further comprises at least one calcium phosphate compound it is likewise possible to achieve an improvement in the growth rate of fluoroapatite. Examples of the suitable calcium phosphate compounds are fluoroapatite, monetite, brushite, amorphous calcium phosphate, hydroxylapatite, etc. The calcium phosphate compound is used preferably in the form of particles and most preferably in the form of spherical or predominantly spherical particles. The size of these particles is preferably 5 to 50 μm, in particular 10 to 20 μm. Appropriately 5 to 30% by weight of calcium phosphate compounds is added to the first gel. In one particularly preferred embodiment the first gel comprises 5 to 30% by weight of predominantly spherical fluoroapatite particles having a size of 5 to 50 μm.

By addition of fluoride ions to the phosphate-containing gel, the resistance of the layer to acids can be increased.

According to the invention, it is possible by means of induced mineralization to regenerate tooth enamel defects. By the use of a two-layer gel which is solid at body temperature and can be applied locally to the affected site on the tooth, and by the use of a mouthwash as a medium containing calcium ions, mineralization conditions are created which bring about the formation of a tooth enamel-like substance which grows directly on the tooth. In the case of the previously published double-diffusion method, it was shown only that fluoroapatite which results by countercurrent diffusion of calcium and phosphate ions in a gelatin gel forms spherical aggregates whose organic proportion by weight corresponds to that of mature, human tooth enamel. The double-diffusion method, however, has neither opened up a possibility of making possible the remineralization of tooth enamel in man nor implied this possibility in any manner. The experimental setup employed in the double-diffusion method brings about the formation of small beads and does not allow the growth of uniform layers of apatite material on a substrate. This is only possible by means of the procedure according to the invention.

It is further possible to regenerate tooth core defects as well by induced remineralization of dentine. In this case dentine layers are formed which grow directly on the tooth material.

The invention can be applied, in particular, in man. It is possible here, for example, to cure relatively small carious defects by induced remineralization or to cover sensitive sites on the tooth with a protective apatite layer. The procedure for treatment here is preferably as follows: The carious site is initially treated with an alkaline medium, e.g. with sodium hydroxide, and then painted with a thin layer of the phosphate-containing gel warmed to approximately 50° C. or this is applied with a suitable syringe, which can be warmed. The gel solidifies immediately on the surface of the tooth and is covered with the protective gel or a medium containing calcium ions according to the same method. 1 to 3 times in the day, an approximately 10-minute mouthwash is then carried out if appropriate with a calcium solution. Instead of the mouthwash, a gel containing calcium ions can also be applied. A 0.1 to 0.5N calcium gel is preferred, for example, which simplifies the application further. Between the washes, the tooth is covered with a suitable cap, which can be made of plastic or metal, such that the patient is not incapacitated and the remineralization can take place undisturbed. If many teeth are affected, the whole row of teeth can also be protected with a guard, such as is employed, for example, against odontoprisis. Every two days, the gel is changed, and at this opportunity the affected tooth is cleaned and disinfected.

According to the invention, a first gel is applied to the tooth material. This gel contains gelatin and phosphate ions and optionally further constituents, in particular calcium phosphates, as explained above. The content of gelatin in the first gel is preferably from at least 15% by weight, more preferably from 25% by weight, up to 40% by weight, more preferably up to 30% by weight. The gelatin, in particular, has a function in the development of the morphology of the apatite formed. It was surprisingly discovered that when using gelatin, an apatite material is deposited on the surface of the tooth material which has a great similarity with native tooth enamel or dentine. When using other organic matrices, however, other morphologies of the apatite crystallizates were observed, such that a building up of apatite on the surface of the tooth material, as desired according to the invention, does not occur.

Gelatine is a polypeptide which can be obtained, in particular, by hydrolysis of the collagen contained in the skin and bone of animals. Gelatine customarily has a molecular weight of 15,000 to over 250,000 g/mol and can be obtained from collagen under acidic or alkaline conditions. According to the invention, the following gelatins are preferably employed: Acid-hydrolyzed gelatin types (type A), e.g. prepared from pigskin or calfskin having a high Bloom value, e.g. 250 to 350 Bloom (the Bloom value is understood as meaning a parameter which characterizes the gel solidity, in general it is true that the higher the Bloom value, the higher the proportion of long-chain molecules in the gelatin and the higher the gel solidity).

Beside gelatin, which is present for the formation of the desired morphology of the apatite and the building up on the surface of the tooth material, the first gel furthermore comprises phosphate ions. These phosphate ions represent a basic constituent of the apatite built up from calcium phosphate. The concentration of the phosphate ions in the first gel is preferably at least 0.01 mol/l, more preferably at least 0.05 mol/l, and up to 0.5 mol/l, more preferably up to 0.2 mol/l, and in particular 0.08 mol/l.

The first gel preferably has a softening temperature which lies above normal body temperature such that the gel is solid at body temperature. The softening temperature of the first gel preferably lies in the range from 38 to 45° C., more preferably from 38 to 42° C. The first gel is preferably applied in warmed form, for example warmed to 45 to 55° C. After applying, the gel cools and becomes solid.

According to the invention, a second gel, a "protective gel", can be applied in a further step. The first gel layer, in particular, is covered with this second gel. The protective gel, which functions as a gel covering layer, surprisingly causes the mineralization, that is the formation of apatite, to take place mainly or exclusively on the surface of the tooth and not on the gel-liquid boundary layer. By means of the two-layer gel construction which is achieved in the process according to the invention, a building up or growth of apatite on the tooth material and not a crystallization or formation of apatite spheres within the gel occurs, as is described in the prior art. By means of the two-layer construction is a practicable and technically useful remineralization of the teeth thus possible.

The pH and the gel concentrations of the second gel typically correspond to those which are indicated herein for the first gel. The second gel also preferably has a softening temperature of 38 to 45° C., in particular of 38 to 42° C. and is preferably applied warmed to 45 to 55° C.

In a third step or instead of the protective gel (in particular in the case of a gel containing calcium ions), a medium containing calcium ions is finally applied. The medium containing calcium ions provides the basic structural material further needed for the formation of apatite, namely calcium ions. These calcium ions diffuse through the protective gel and the first gel layer as far as the surface of the tooth material and are deposited there as apatite. The concentration of the calcium ions in the medium containing calcium ions is preferably at least 0.01 mol/l, more preferably at least 0.05 mol/l, and up to 0.5 mol/l, more preferably up to 0.2 mol/l, and in particular 0.13 mol/l.

It was discovered that according to the invention a uniform layer of apatite crystallites which are parallel or grown in rays can be formed. Furthermore, this layer exhibits no peripheral gap or only a submicrometer-large peripheral gap to the native tooth material. The direction of growth of the apatite crystallites takes place perpendicular to the substrate, independently of the orientation of the enamel prisms, such that on suitable orientation of the enamel prisms the longitudinal orientation of the artificially grown crystals proceeds substantially identically to the crystals in the prisms. The order of magnitude of prism crystals and grown fluoroapatite is identical. Within the layers, a tight and uniform packing can be observed. Furthermore, the apatite layer applied has a Vickers hardness which corresponds to that of the native tooth enamel. The apatite layers applied according to the invention in particular have a Vickers hardness in the range from 250 to 400 HV.

According to the invention, it is possible to apply apatite layers in any desired thickness, since the layer thickness achieved is dependent on the frequency of the change of gel. Growth rates of from 1 to 5 μm/day, in particular from 3 to 5 μm/day can be achieved with the process according to the invention.

In a preferred embodiment, a gelatin-glycerol gel is employed as the first gel. The weight ratio of gelatin to glycerol is preferably 1:5 to 5:1 here, in particular 1:2 to 2:1. Glycerol has the effect that the softening point of the gel is raised above the normal human body temperature. The gel solidity achieved is necessary in order to obtain the two-layer system during the mineralization such that a specific, controlled crystal deposition is made possible. In a liquid gel, a spontaneous precipitation of finely crystalline material would occur, which does not grow on the tooth.

The first gel preferably furthermore contains fluoride ions. The fluoride can be added, for example, as sodium fluoride or ammonium fluoride. In this embodiment, fluorine-rich apatite or fluoroapatite can be grown on the surface of the tooth material. Fluoroapatite is, in particular, more acid-resistant than the carbonate-containing hydroxyapatite of the natural tooth enamel, the morphology of the layers of fluoroapatite forming nevertheless having a great similarity to native tooth enamel.

The growth rate of the apatite or fluoroapatite is determined, inter alia, by the pH of the first gel. Preferably, the first gel has a pH of 2.0 to 6.0, in particular of 4.0 to 6.0, more preferably of 5.0 to 5.5.

Furthermore, a protective gel or a gel containing calcium ions is used as the second gel. The first gel layer containing phosphate ions is covered with this gel. By use of this gel layer, surprisingly the apatite formation takes place exclusively on the surface of the tooth material and a spontaneous crystallization of apatite crystallites or composite aggregates does not occur, such as is observed in the case of the procedures known in the prior art. In contrast to the investigations with double-diffusion chambers, a coating of tooth material surfaces can thus be obtained in a controlled manner. While the second gel preferably contains no materials which are to be incorporated into the apatite, and is thus, in particular, free of phosphate ions, calcium ions and/or fluoride ions, it is possible, in certain embodiments, to apply a gel containing calcium ions as the second gel. Growth rates of several μm per day were also achieved with it. Gelatine can likewise be employed for the formation of the second gel, a gelatin-glycerol gel being preferred. The second gel used can, however, also be another gel, e.g. selected from polysaccharides, for example agarose or carrageenan, and also carboxymethylcellulose.

The tooth material coated with a first gel and optionally protective gel can finally be treated with a medium containing calcium. The medium containing calcium employed can be, for example, a solution containing calcium ions and/or a gel containing calcium ions. The medium containing calcium ions is preferably prepared here using a water-soluble salt containing calcium ions, for example from $CaCl_2$.

The medium containing calcium ions preferably has a pH of 6 to 8.

According to the invention, the two constituents of apatite, namely phosphate ions and calcium ions, are in each case separately supplied as an individual component, the calcium phosphate formation taking place on the tooth material surface.

In order to prevent a local overacidification on the mineralization front by means of the proton release during the apatite formation, the phosphate gel is preferably treated with a buffer system, preferably an acetic acid buffer or α,α,α-tris (hydroxymethyl)methyl-amine buffer.

Before the treatment with the alkaline medium or/and with the first gel, the tooth material can be pretreated, in particular defatted, slightly etched or/and rinsed. For example, for better efficacy the tooth surface can initially be defatted with ethanol and slightly etched with phosphoric acid and subsequently rinsed with deionized water.

The process according to the invention is suitable, in particular, for the treatment of human teeth or tooth enamel. Various defects can be treated here by remineralization or else the tooth material can also be covered prophylactically with a protective apatite or fluoroapatite layer. The apatite layers are formed both on tooth enamel and on dentine as a substrate.

The invention furthermore relates to a composition and/or a kit which, in particular, is suitable for the use described above and comprises
a) an alkaline medium,
b) a first gel which comprises gelatin and phosphate ions, and
c1) a second gel which is free of phosphate ions, or/and
c2) a medium containing calcium ions.

The preferred embodiments of the constituents are as described above here.

The invention is further illustrated by the following examples.

EXAMPLES

Example 1

Comparative Example

Step 1. Preparation of the Tooth Material

A human tooth (arbitrary) was separated from its root and the crown was sawn into disks approximately 0.5 mm wide. The disks were immersed for 30 s in a 30% strength phosphoric acid solution, washed with deionized water and dried.

Step 2. Preparation of the Gel

A homogeneous gel whose pH was 5.0 was prepared at 80° C. with stirring from 8.56 g of gelatin, 8.24 g of 85% strength glycerol solution, 7.26 g of $H_2O$, 1.8 ml of 2N NaOH, 2.7 ml of 2N HAc, 13.8 mg of NaF and 236 mg of $Na_2HPO_4$. A further gel was prepared from 8.56 g of gelatin, 8.24 g of 85% strength glycerol solution and 11.76 g of $H_2O$. A 0.133 molar calcium solution was prepared from $CaCl_2$ salt.

Step 3. Induced Mineralization on the Tooth Surface

The surface of the tooth disks was painted with approximately 0.5 ml of the phosphate-containing gel. After its solidification, covering was carried out with approximately 0.5 ml of the additive-free gel. The tooth disk was inserted into a plastic tube closed on one side and stored at 37° C. in a calcium solution. The gel and the solution were renewed every 7 days, altogether 16×. For the appraisal of the layer grown, a fracture of the sample perpendicular to the cut surface was carried out in order to be able to measure the layer thickness. As the SEM in FIG. 1 confirms, a uniform layer of elongated crystallites having a layer thickness of 7.2 μm is formed. This corresponds to a growth rate of approximately 450 nm/week.

Example 2

The procedure is carried out analogously to example 1, but first of all a treatment with an alkaline solution was carried out. Moreover, storage took place in calcium solution, as described above, or in SBF (Simulated Body Fluid with 142 mM $Na^+$, 5 mM $K^+$, 15 mM $Mg^{2+}$, 25 mM $Ca^{2+}$, 148.8 mM $Cl^-$, 4.2 mM $HCO_3^{2-}$, 1 mM $HPO_4^{2-}$, 0.5 mM $SO_4^{2-}$) or dry. Growth rates were observed of 0.9 to 1.4 μm/day in the case of dry storage, of 1.4 to 1.9 μm/day in the case of storage in SWF, and of 2.1 μm/day on storage in a Ca solution. Layer formation took place preferentially on dentine.

Example 3

The procedure corresponds to example 2. However, fluoroapatite spherulites with a diameter ≤20 μm, a diameter of 20 to 25 μm or a diameter of 50 to 100 μm were added to the first gel. It was possible here to obtain growth rates of 5 μm/day for the addition of fluoroapatite spherulites having a diameter of ≤20 μm, a growth rate of 4 μm/day for the addition of fluoroapatite spherulites having a diameter of 20 to 25 μm, and a growth rate of 1.25 μm/day for the addition of fluoroapatite spherulites having a diameter of 50 to 100 μm.

Example 4

The procedure corresponds to example 2, using a calcium gel instead of the calcium solution. Here as well it was possible to ascertain comparable growth rates.

Example 5

The procedure corresponds to example 4, the protective gel being omitted. Here again, growth rates of 1.8 to 5 μm/day were obtained

The invention claimed is:

1. A composition for the growth of apatite, fluoroapatite, or dentine on tooth material, comprising
    (a) a pre-treating alkaline medium comprising calcium ions,
    (b) growth-promoting components i, ii, and iii:
        i. a first gel comprising gelatin and phosphate ions,
        ii. a second gel, which is free of phosphate ions and calcium ions, capable of covering a first layer of said first gel with a layer of the second gel, and
        iii. a growth-promoting solution containing calcium ions,
    wherein said pre-treating alkaline medium and each of said components are kept separate until use of said composition.

2. The composition of claim 1, wherein the first gel further comprises at least one calcium phosphate compound.

3. A multi-component composition for growing biomimetic apatite, fluoroapatite or dentine on tooth material, comprising
    (i) an alkaline pre-treating component comprising calcium ions,
    (ii) a first gel comprising gelatin and phosphate ions, and
    (iii) a second gel which is free of phosphate ions and contains calcium ions, which is capable of covering a first layer of the first gel with a layer of this second gel,
    wherein said second gel is effective for locally separating reactive ions in said composition to effect said growth of biomimetic apatite, fluoroapatite or dentine on said tooth material.

4. The composition of claim 1, wherein the alkaline medium is an alkaline solution or an alkaline gel.

5. The composition of claim 1, wherein the alkaline medium has a pH of 7.1 to 14.

6. The composition of claim 1, wherein the alkaline medium comprises 0.05 to 1N NaOH.

7. The composition of claim 1, wherein the first gel is a gelatin-glycerol gel.

8. The composition of claim 1, wherein the first gel further comprises fluoride ions.

9. The composition of claim 1, wherein the first gel has a pH of 2.0 to 6.0.

10. The composition of claim 2, wherein the calcium phosphate compound is selected from the group consisting of fluoroapatite, monetite, brushite, amorphous calcium phosphate, and hydroxylapatite.

11. The composition of claim 2, wherein the calcium phosphate compound is fluoroapatite.

12. The composition of claim 11, wherein the fluoroapatite is in the form of spherical particles.

13. The composition of claim 2, wherein the first gel contains 5 to 30% by weight of calcium phosphate compounds.

14. The composition of claim 13, wherein said calcium phosphate compounds are fluoroapatite particles.

15. The composition of claim 2, wherein the first gel contains spherical particles of calcium phosphate compounds.

16. The composition of claim 15, wherein said calcium phosphate compounds are spherical particles of fluoroapatite.

17. The composition of claim 2, wherein the calcium phosphate compound comprises particles having an average size of 5 to 50 μm.

18. The composition of claim 17, wherein the average size of said particles is 10 to 20 μm.

19. The composition of claim 1, wherein the second gel is also free of fluoride ions.

20. The composition of claim 1, wherein the second gel is selected from the group consisting of gelatin-glycerol gels, polysaccharide gels and carboxymethyl-cellulose gels.

21. The composition of claim 1, wherein the solution containing calcium ions has a pH of 6 to 8.

22. The composition of claim 1, wherein said tooth material is human teeth or human tooth enamel.

23. A kit for the growth of apatite, fluoroapatite, or dentine on tooth material, comprising
    a) a pre-treating alkaline medium comprising calcium ions,
    b) growth promoting components i, ii, and iii:
        i. a first gel which comprises gelatin and phosphate ions,
        ii. a second gel, which is free of phosphate ions and calcium ions, capable of covering a first layer of said first gel with a layer of this second gel, and
        iii. a growth-promoting solution containing calcium ions
wherein said pre-treating alkaline medium and each of said components are provided separately in said kit,
    the kit further comprising instructions for:
        (I) first treating tooth material with said pre-treating alkaline medium comprising calcium ions, thereafter
        (II) next applying the first gel to said tooth material, and thereafter
        (III) applying the second gel by covering the first gel with a layer of the second gel, and thereafter
        (IV) applying the growth-promoting solution containing calcium ions to said tooth material.

24. A process for the growth of apatite, fluoroapatite, or dentine on tooth material, comprising the steps
    (i) treating said tooth material with a pre-treating alkaline medium comprising calcium ions, thereafter
    (ii) applying a first gel which comprises gelatin and phosphate ions to said tooth material, and thereafter
    (iii) applying a second gel which is free of phosphate ions and calcium ions for covering a first layer of the first gel with a layer of this second gel, and thereafter
    (iv) applying a growth-promoting solution containing calcium ions to said tooth material,
wherein said application steps are effective in causing a building up of apatite, fluoroapatite, or dentine on the surface of the tooth material.

25. A kit for the growth of apatite, fluoroapatite or dentine on tooth material, comprising
    (i) a pre-treating alkaline medium comprising calcium ions,
    (ii) a first gel which comprises gelatin and phosphate ions, and
    (iii) a second gel which is free of phosphate ions and contains calcium ions, which is capable of covering a first layer of the first gel with a layer of this second gel, wherein said second gel is effective for locally separating reaction ions to effect said growth of biomimetic apatite, fluoroapatite or dentine on said tooth material, and
wherein said pre-treating alkaline medium and each of said first gel and second gel are provided separately in said kit,
    the kit further comprising instructions for:
        (I) first treating tooth material with a pre-treating alkaline medium comprising calcium ions, thereafter
        (II) next applying the first gel to said tooth material, and thereafter
        (III) applying the second gel by covering the first gel with a layer of the second gel.

26. A process for the growth of apatite, fluoroapatite or dentine on tooth material, comprising the steps
    (i) treating said tooth material with a pre-treating alkaline medium comprising calcium ions, thereafter
    (ii) applying a first gel which comprises gelatin and phosphate ions to said tooth material, and thereafter
    (iii) applying a second gel which is free of phosphate ions and contains calcium ions for covering a first layer of the first gel with a layer of this second gel,
wherein said application steps are effective in causing a building up of apatite, fluoroapatite or dentine on the surface of the tooth material.

* * * * *